United States Patent [19]
Golden

[11] Patent Number: 5,827,748
[45] Date of Patent: Oct. 27, 1998

[54] CHEMICAL SENSOR USING TWO-DIMENSIONAL LENS ARRAY

[75] Inventor: Joel P. Golden, Fort Washington, Md.

[73] Assignee: The United States of America as represented by the Secretary of the Navy, Washington, D.C.

[21] Appl. No.: 787,720

[22] Filed: Jan. 24, 1997

[51] Int. Cl.$^6$ .............................................. G01N 33/552
[52] U.S. Cl. ........................... 436/527; 435/7.1; 435/7.9; 435/968; 435/970; 435/973; 436/518; 436/172; 436/807; 436/809; 436/806; 422/82.05; 422/82.07; 422/82.08; 422/82.11
[58] Field of Search ............................ 422/82.05–82.11; 435/7.1, 7.9, 968, 970, 973; 436/518, 172, 807, 809, 527, 806

[56] References Cited

U.S. PATENT DOCUMENTS

| | | | |
|---|---|---|---|
| 5,015,844 | 5/1991 | Cole | 250/227.24 |
| 5,089,387 | 2/1992 | Tsay et al. | 435/6 |
| 5,096,807 | 3/1992 | Leaback | 435/6 |
| 5,255,075 | 10/1993 | Cush | 356/445 |
| 5,565,978 | 10/1996 | Okubo et al. | 356/128 |
| 5,584,982 | 12/1996 | Dovichi et al. | 204/603 |
| 5,606,170 | 2/1997 | Saaski | 250/458.1 |
| 5,639,671 | 6/1997 | Bogart et al. | 436/518 |
| 5,653,939 | 8/1997 | Hollis et al. | 422/50 |

FOREIGN PATENT DOCUMENTS

723 146 A1  7/1996  European Pat. Off. .

*Primary Examiner*—Carol A. Spiegel
*Attorney, Agent, or Firm*—Thomas McDonnell; Barry A. Edelberg

[57] ABSTRACT

A chemical sensor includes a patterned layer having discrete sections, a two-dimensional detector array, and a two-dimensional lens array that focuses an optical signal from the patterned layer onto the two dimensional detector array. Typically, the two-dimensional detector array is a charge-coupled device array and the lens array is a graded index of refraction lens array. The chemical sensor maintains good resolution throughout its field of view.

15 Claims, 2 Drawing Sheets

CHEMICAL SENSOR USING TWO-DIMENSIONAL LENS ARRAY

BACKGROUND OF THE INVENTION

1. Field of the Invention

The present invention relates generally to chemical sensors and more specifically to multi-analyte chemical sensors employing arrayed charge-coupled imaging devices.

2. Background of the Invention

Multiple-analyte-detecting chemical sensors, particularly biochemical sensors, have been previously described. In some embodiments, these sensors include a patterned layer including discrete sections, and a light sensor array (e.g., a charge-coupled device (CCD) array or a photodiode array). Each discrete section, in response to the presence in a sample of an analyte of interest, alters light transmitted through, absorbed by, or emitted from that section. In some cases (e.g., sandwich assays), this response appears only after the reaction with a third, labelled molecule). Each section is specific for a single analyte. Light from the patterned layer is then transmitted, typically through an appropriate filter, to a sensor array. The light sensor array produces an image or electrical signal that can then be correlated with the patterned layer to simultaneously determine the presence of a variety of analytes.

Typically, it is desirable to perform multiple-analyte chemical and biochemical detection in the field. Field use requires a compact, light-weight device that may be easily transported and used. Thus, a high density of sections in the patterning layer is desirable. The need for good resolution between optical signal from nearby sections (to prevent optical signals from nearby sections from overlapping at the light sensor array layer), however, limits the usable density of sections. A lens improves resolution, and thus usable density, but only for a small portion of the field of view.

SUMMARY OF THE INVENTION

Accordingly, it is an object of this invention to chemically detect multiple analytes using a small, compact sensor.

It is another object of the present invention to enhance the usable density of discrete sections throughout the field of view in a patterned layer of a multiple analyte chemical sensor.

It is a further object of the present invention to enhance the optical resolution between signals from nearby sections throughout the field of view in the patterned layer of a multiple-analyte chemical sensor that detects those signals using a two-dimensional light sensor array.

These and other objects are accomplished by using a two-dimensional lens array to focus optical signals from discrete sections in the patterned layer of a multiple-analyte sensor onto a two-dimensional light sensor array.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

The responses were determined from the subtracted images for each concentration obtained as described in the "EXAMPLES" section below. The average fluorescence intensities for each of the three circular regions was averaged and normalized to the average intensities from the rectangular regions for the row of interest. Data shown are for (○) rabbit anti-goat IgG, (□) rabbit anti-chicken IgG, and (Δ) rabbit anti-mouse IgG.

DESCRIPTION OF THE PREFERRED EMBODIMENTS

The sensor of the present invention is a multilayered device. The outer, exposed layer of the device has a plurality of discrete sensing sections formed in a two-dimensional pattern on the surface of the layer. Each of these sensing sections, in the presence of a specific analyte, provides a detectable optical signal. Different sensing sections within the patterned surface are specific for different analytes. Thus, a plurality of different analytes within a sample contacted with the sensing layer may be simultaneously detected.

The selection of material for use as the sensing layer is not critical to the advance achieved according to the present invention. Any materials useful as the sensing surface in conventional multiple-analyte sensors may be used according to the present invention. For example, sensing surfaces useful in the method of the present invention may be flat glass or plastic surfaces. Typically, and conveniently, the sensing surface is the upper surface of a waveguide substrate, such as a glass coverslip. Throughout the present specification and the claims that follow, a waveguide substrate is defined as a material that acts both as a substrate for the pattern and as a medium for the excitation light and/or light emitted from or transmitted through the pattern. The low cost, light weight, and disposability of glass coverslips make them particularly advantageous as waveguide substrates for use in portable chemical and biochemical sensors.

Figure 1:
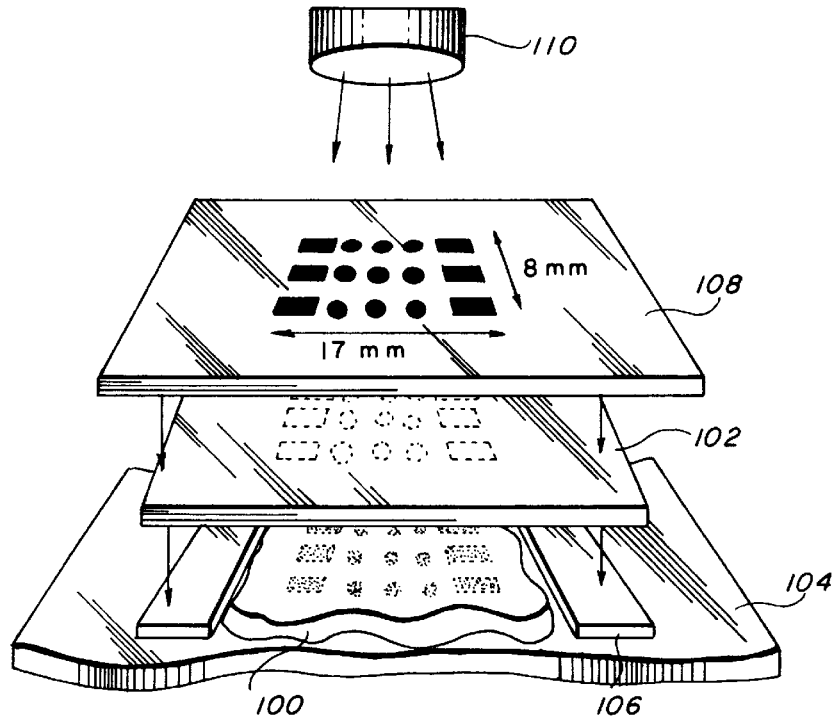
FIG. 1 illustrates the construction of antibody pattern on a coverslip for use with the present invention.

A pattern of sensing sections may be formed in the sensing surface by any method, including conventional methods. Typically, and as shown in FIG. 1, layer 100 of photopolymerizable optical adhesive is applied between glass coverslip 102 and wax film layer 104 (for example, PARAFILM) coated unto a suitable material, such as glass. TEFLON (tetrafluoroethylene) or other non-adherent spacers 106 space coverslip 102 from the PARAFILM coating. This assembly is exposed, through photomask 108, to photopolymerizing uv radiation from light source 110. The PARAFILM and unexposed portions of the adhesive layer are then removed, leaving behind wells formed within a layer of moderately polymerized adhesive, with the glass coverslip forming the bottom of the wells. The bottom of these wells is then silanized to allow crosslinking to antibodies or other molecules or biomolecules that specifically react with an analyte of interest.

Biospecific, or chemically-specific, molecules are then added to each well, for example with a pipette, micropipette or similar dispenser. Each well may be filled with a molecule specific to a different analyte. The moderately polymerized polymer layer is then removed, by conventional methods, to expose the remainder of the coverslip. The newly exposed areas of the coverslip are then blocked to prevent non-specific binding thereto.

The optical signal obtained in the presence of the analyte may be either an increase or a decrease in the light emitted by a section. Typically, the optical signal is either an increase or decrease in the fluorescence emitted from the section to which the analyte of interest has bound. Phosphorescence and other luminescent phenomena may also be used as the optical signal. Whether optical signal obtained is directly or inversely proportional to the concentration of an analyte of interest will depend largely, and in a known manner, upon the type of assay performed, e.g., competitive assay, sandwich assay, direct assay, or displacement assay.

The type of assay performed will also determine, in a known manner, which, if any, molecules are labelled. The present invention may be used in any type of immunoassay using an optical signal to indicate the presence of an analyte of interest. These assays include direct assays, competitive assays, displacement assays, and sandwich assays. In most competitive assays, an antibody to the analyte is attached (typically covalently) to the supporting surface. During the assay, free, unlabelled analyte and a labelled analog of the analyte having essentially the same immunoreactivity as the analyte compete for free analyte-binding sites on the attached antibody. In a typical displacement assay, the analyte-binding sites on the support-attached antibody are saturated with a labelled analog of the antigen. The support is then briefly contacted with the analyte. Some of the unlabelled analyte displaces some of the bound, labelled analyte. In a typical sandwich assay, one immunoreactive molecule (typically, an unlabelled antibody), is attached (typically covalently) to a support surface. The support surface is then allowed to react with and bind unlabelled analyte from the sample. Then, a labelled antibody is reacted with the bound, unlabelled analyte. In the specification and the claims the follow, a molecule and the labelled analog of that molecule have essentially the same immunoreactivity toward their binding partner (i.e., the labelled analog and the unlabelled molecule are immunoequivalent) if, for the purposes of the assay being performed, the differences in reactivity are insignificant. However, labelling may not always be required. For example, if specific interaction of the attached molecule and the analyte of interest forms a fluorescent molecule, or quenches fluorescence emitted from a molecule attached to a section of the pattern, labelling may not be required.

Figure 2:
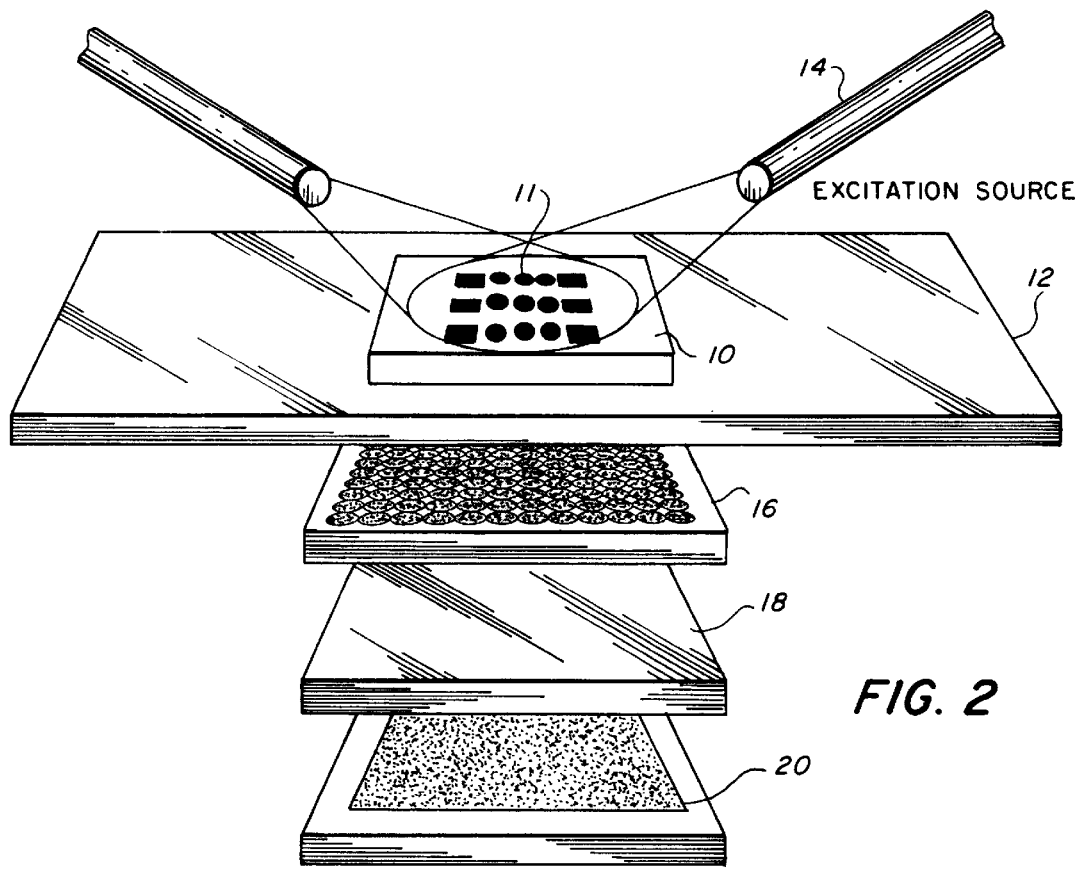
FIG. 2 is an exploded view showing a typical apparatus according to the present invention.

As shown in FIG. 2, this coverslip 10, with pattern 11 thereon, is then placed on transparent support 12 (typically glass or clear plastic window) of an imaging device and exposed to a sample (not shown). Typically, gravity maintains coverslip 10 in place on support 12. If necessary for light emission from pattern 11, pattern 11 is exposed to a source of excitation light 14. Transparent support 12 transmits light from the coverslip 11 to two-dimensional lens array 16. Generally, this transmitted light will be a combined light that includes both excitation light and the optical signal from the signal patterning layer.

Two-dimensional lens array 16 is sandwiched between transparent support 12 and optical emission filter 18, and focuses light from pattern 11 onto imaging array 20, which supports filter 18.

Focusing light emitted from pattern 11 with a lens array, rather than a single lens, greatly reduces aberration. Consequently, lens array 16 greatly enhances the resolution in the imaging array. Because of this enhanced imaging resolution, the present invention permits a higher useful patterning density, and a more compact design, than available in analogous prior art sensors.

Any two-dimensional lens array may be used in the present invention. Because of its flat surface and profile, a two-dimensional graded index of refraction (GRIN) lens array is particularly advantageous for use according to the present invention. Also, GRIN lens arrays with small focal lengths may be inexpensively produced. Nevertheless, other types of lens arrays, including concave lens arrays, may be used in place of GRIN lens arrays. Also, a two-dimensional lens array may be molded in to the substrate support.

The use of a patterned coverslip 10 is optional. If desired, pattern 11 of sections that specifically recognize various analytes of interest may be placed directly on the glass support 12. The disposability of patterned coverslip 10, however, provides convenience and cost benefits. Alternatively, slides, or capillary tubes having a flattened longitudinal surfaces upon which the desired pattern is formed, may be used in place of coverslips. Where the waveguide support is a capillary tube(s) or other hollow structure(s), the excitation light may be launched into the interior of the hollow structure (i.e., an evanescent excitation wave).

Emission filter 18 removes the excitation light from optical signals transmitted through lens array 16. Preferably, this filter is positioned (as shown in FIG. 2) between the lens array and the imaging array to reduce scattering. Positioning filter 18 between glass support 12 and lens array 16 would increase scattering, in unfocusing the desired image.

Any filter may be used as filter 18. Typically, filter 18 is an absorptive long-pass filter. An alternative is to use an interference filter, which would have a narrow blocking band and potentially allow more of the optical signal through. However, an interference filter usually requires collimated light. This collimation can be achieved by using two 2-d lens arrays, with the first one collimating the light and the second focusing onto the CCD. Placing the filter in between two lens arrays allows the use of interference filters.

The present invention may be incorporated into multianalyte biosensors for many antigens, including biologically hazardous agents, environmental pollutants, explosives, or drugs of abuse (see Ligler et al., *Immunomethods* 3, 122–127 (1993); Shriver-Lake et al., *Sensors and Actuators B* 11, 239–243 (1993); and Shriver-Lake et al., *Anal. Chem.* 34, 2431–2435 (1995), the entireties of which are incorporated herein by reference for all purposes) Additionally, the present invention can easily detect antibody concentrations as low as 50 ng/mL (0.29 nM for ~170 kD antibody analytes).

Having described the invention, the following examples are given to illustrate specific applications of the invention including the best mode now known to perform the invention. These specific examples are not intended to limit the scope of the invention described in this application.

EXAMPLES

Materials and Methods

Imaging system

The basic design of the biosensor is shown in FIG. 2, which was discussed above. A scientific grade CCD image sensor (CCD05-30 from EEV, Elmsford, N.Y.) consisting of 1242 (H)×1152 (V) pixels was used as the detection system. This CCD was operated in inverted (MPP) mode to suppress dark current noise. CCD detectors operated in this mode acquire dark current noise up to 20-fold less quickly than non-MPP CCD's, and improve charge transfer efficiency. The combined effect is that for relatively short exposures, these CCDs can be operated at room temperature with significant sensitivity. Half of the vertical pixels were used as a framestore for continuous image acquisition, so each image frame consisted of 1242 (H)×576 (V) pixels. The readout rate (pixels/sec) was maintained at 50 KHz, so that each image took 14.8 sec to acquire.

The glass-covered CCD chip was inserted into an appropriate headboard and mounted underneath a metal stage. The output video signal from the chip and electrical power was controlled by drive circuitry unit (EEV, Elmsford, N.Y.) external to the stage area. The video output signal was collected using a Lab-LC A/D board (National Instruments, Austin, Tex.) mounted in a Macintosh LC475 computer, and a program written in THINK C using the A/D board software libraries. Each acquired frame was saved as a 12-bit digital image.

The stage area above the CCD was constructed from a 0.6 cm thick rectangular aluminum plate with dimensions 21 cm×26 cm. This plate was mounted on four 15.2 cm screws (one at each corner of the plate) and secured to an optical breadboard. A rectangular area 10.1 cm×8.3 cm was removed from the aluminum plate near its center. A 0.2 cm wide and 0.2 cm deep ledge was cut into the aluminum plate around the rectangular cutout, such that a large glass microscope slide (10.2 cm×8.3 cm×0.2 cm (Thomas Scientific)) just fit into the cutout and was flush with the top of the aluminum plate. The bottom of the glass plate was masked with black spray paint, except for a region in the center with dimensions 3.5 cm×7.3 cm. The glass coverslips with immobilized antigens (see below) were placed over the unpainted region for interrogation.

A graded index of refraction (GRIN) lens array was placed beneath the glass plate to focus the surface of the cover slips onto the CCD. Each cylindrical GRIN lens was 0.7 cm long, with a diameter of 0.09 cm and a focal length of 0.38 cm from either end of the lens cylinder. The two-dimensional GRIN lens array was constructed from linear rows of GRIN lenses (Nippon Sheet Glass, Summerset, N.J.) so that it covered the unmasked area under the glass plate. The array was mounted 3 mm below the glass plate and 3 mm above the CCD surface, with the heights adjusted to achieve exact focusing.

The coverslips were interrogated by projecting two beams of light from a halogen projector lamp equipped with two fiber-optic bundles (Dolan-Jenner Industries, Lawrence, Mass.) through two 635±10 nm bandpass filters (Omega Optical, Brattleboro, Vt.) and onto the coverslip surface. Light was projected at a 45° angle from the coverslip surface, and was introduced from two sides to improve lighting homogeneity. A 5 cm×5 cm square 665 nm long pass filter (Schott Glass, Duryea, Pa.) was placed between the GRIN lens array and the CCD to reduce detection of excitation light.

Construction of Antibody Arrays

Antibody arrays were formed on glass coverslips (22×40 mm, No. 1.5; VWR Scientific, Media, Pa.) by generating a series of wells using the photomask shown in FIG. 1. The mask was constructed by printing the pattern onto standard overhead projector transparencies. This mask consisted of 6 rectangular regions that served as control wells for lighting variations and 9 circular regions.

Wells were formed by placing a 0.2 mm layer of Norland Optical adhesive no. 63 (Norland Products, Brunswick, N.J.) between the glass coverslip and a layer of laboratory PARAFILM laboratory film. The pattern was then placed over the glass and unfiltered light from a 100 W xenon lamp was directed onto the pattern for two minutes, as per the manufacturer's directions for pre-curing. The pattern and PARAFILM laboratory film were then removed to expose the moderately polymerized adhesive. An acetone soaked cotton swab was used to remove unpolymerized adhesive from the wells. This left polymer-free wells with glass bottoms within the polymerized coating. The cleaned coverslip with polymer were placed under a 360 nm UV lamp (Fisher Scientific) for thirty minutes. The fully cured polymer on glass was stored overnight in the dark.

The polymer coated glass coverslips were then silanized to activate the wells for crosslinking to antibodies, using the method described in Bhatia et al., Anal. Biochem. 178, 408–413 (1989), the entirety of which is incorporated herein for all purposes. The coverslips were coated with a 4% solution of 3-mercaptopropyltrimethoxysilane (Fluka) in toluene. The silanized coverslips were then incubated with 2 mM g-maleimidylbutyryl succinimide (Fluka) in ethanol for 1 hr. prior to the addition of antigen.

The following immunoglobulins were purchased from Jackson ImmunoResearch (West Grove, Pa.): Horse IgG, Cy5-labeled rabbit anti-horse, goat IgG, Cy5-labeled rabbit anti-goat, chicken IgG (IgY), Cy5-labeled rabbit anti-chicken, mouse IgG, and Cy5-labeled rabbit anti-mouse. A 0.25 mg/mL solution of each IgG in phosphate buffered saline (PBS) was pipetted into separate wells. The horse IgG was placed into the rectangular wells to serve as the control sample. The goat, chicken, and mouse IgG's were placed in the three wells in each row, so that each measurement could be made in triplicate. After incubating with these antibody solutions for one hour, the coverslips were rinsed with distilled water and stored in 1.5% bovine serum albumin (BSA) in PBS at 4° C.

Immunoassays

Direct immunoassays were performed using Cy5-labeled rabbit anti-species IgG diluted in PBS/0.05% TWEEN-20 surfactant detergent (to reduce non-specific binding of antibodies) to the desired concentrations. The polymer coating that formed the wells during antigen deposition was easily removed from the coverslips after soaking the coverslips overnight in BSA-PBS. These exposed coverslips, with antigens immobilized at specific locations, were immersed in 1.5% BSA for 20 min to block newly exposed, non-specific binding locations on the glass surface.

After BSA blocking, the coverslips were rinsed with distilled water and air dried. A PAP Pen (wax in toluene; The Binding Site Inc., San Diego, Calif.) was used to encircle the assay area to reduce the volume of sample required for the experiment. The coverslips were then secured over the transparent area of the glass plate in the imaging platform.

Images of the coverslips in PBS buffer solutions were taken as background images to be subtracted from the immunoassay images. A 150 µL aliquot of 500 ng/mL Cy5-rabbit anti-horse IgG was initially applied to the coverslip. After 15 min, this solution was rinsed off, the slide illuminated, and an image captured to visualize the rectangular areas on the coverslip. The variation in fluorescence between these rectangular areas accounted for lighting non-uniformity within the image. For increasing concentrations of Cy5-labeled rabbit anti-species IgG, a 150 µL aliquot of each solution was placed on top of the coverslip and allowed to incubate for 15 min. The slide was then rinsed twice with PBS-0.05% TWEEN-20, and the coverslip was illuminated with the halogen lamp. The fluorescence from the bound Cy5-labeled antibody was then visualized by capturing the image. Higher concentrations were added sequentially to generate a titration curve. Species were added in the order: rabbit anti-goat IgG, rabbit anti-chicken IgG, and rabbit anti-mouse IgG.

The amount of antibody captured was quantitated from the CCD images using NIH Image (National Institutes of Health, Bethesda, Md.). Each 12-bit image was linearly scaled to 8-bits for processing, and were well within the dynamic range of the CCD. The areas of interest corresponding to each spot on the coverslip were extracted using a binary mask in the form of the photomask (see FIG. 2). The average fluorescence from each of the three circular areas in each row were computed using the quantitation tools in NIH Image, and the average of these 3 values was used as the initial signal from the region (±standard deviation). The rectangular areas at the end of each row were used as a standardization signal by taking the average intensity of each rectangle and obtaining the norm of the two values. The signals from each of the circular regions were then expressed relative to the norm from the rectangular signals. Since the illumination sources for the images were directed parallel to the rows, and since the rows contained the areas of interest, the greatest need for correction for variation in lighting intensity was in the horizontal direction.

Experimental Results

These experiments show the detection of low concentrations of three Cy5-labeled antibodies, as well as the signal from a fourth labeled antibody used for correcting for uneven illumination. The Cy5-rabbit anti-horse IgG (500 ng/mL) bound to the rectangular regions at the edges of the pattern. The resulting fluorescence (after subtraction of a PBS background) indicated non-uniform lighting across the sample, and in particular, the central horizontal row of antibodies would be expected to be excited to a greater extent than those of either the top or bottom rows. Thus, for quantitation of samples, it is helpful to have such continuous controls in the array.

These experiments also indicate a degree of cross-reactivity between the Cy5-rabbit anti-horse IgG antibody and goat IgG. When examined separately, the other antibodies used did not show detectable cross-reactivity (data not shown). This background reactivity must consequently be subtracted from the specific signals detected.

These experiments also show the sequential addition of 300 ng/mL samples of Cy5-labeled rabbit anti-goat IgG, rabbit anti-chicken IgG, and rabbit anti-mouse IgG. Even at these relatively low concentrations of antigen, excellent sensitivity was observed, and each signal could be easily discerned, with a signal difference of 10–30 standard deviations above background noise levels. Typically, the 50 ng/ml fluorescence intensities were 17–23% higher than the PBS background, and 6–8 standard deviations above background noise following PBS image subtraction. This assay could also detect mixtures of labeled rabbit anti-species solutions at concentrations of 100 ng/mL (data not shown), making it a simple and rapid device for detecting multiple analytes within a single 150 $\mu$L sample.

Due to the linear response of CCD sensors, quantitation of analyte concentrations could also be performed. Increasing concentrations of Cy5-labeled antibody were placed over the coverslip array and allowed to stand for 15 min. After washing, the images due to fluorescence of Cy5 were collected, and the initial image captured prior to addition of the antibody was subtracted from the image for each concentration. The resulting subtracted images for 100 ng/mL solutions of the three Cy5-labeled rabbit anti-species; indicated, as in the prior case, that the signals from the top and bottom rows are less intense than those in the middle. This is in part due to uneven illumination, but may also contain contributions from the varying avidities of the antibodies.

Figure 3:
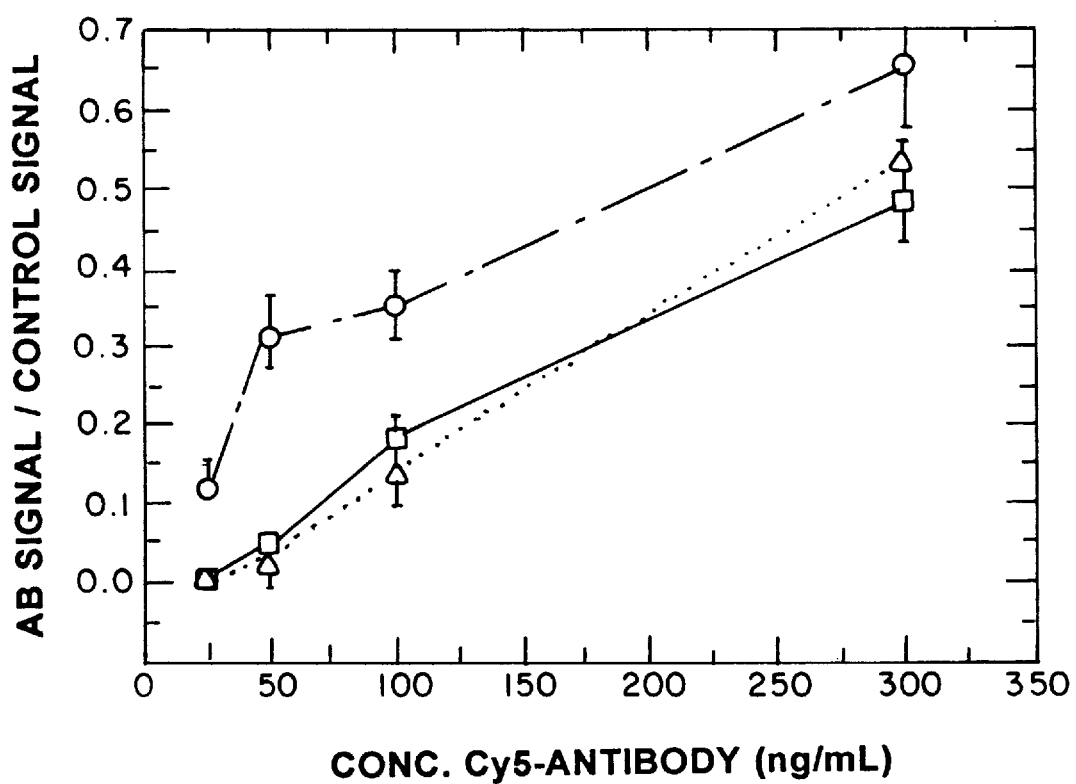
FIG. 3 is a graph showing the response of a biosensor according to the present invention to Cy5-labeled antibody.

The average fluorescence signals from the indicated spots were quantitated with NIH Image for 25, 50, 100, and 300 ng/mL (~0.2–1.9 nM) samples of antibody solutions. These values were then normalized to the average fluorescence from the rectangular regions of the same row in the image (we assume a smooth gradation of lighting intensities across the rows). The normalized data is plotted in FIG. 3 to show the concentration response by the sensor. For both Cy5-labeled rabbit anti-chicken IgG and rabbit anti-mouse IgG, the signal from the 25 ng/mL solution was below the detection limit of the system, while the 50 ng/mL signal was significantly above background. For the coverslip examined in the two above-discussed cases, even in the presence of background Cy5-rabbit anti-horse IgG signals, Cy5-labeled rabbit anti-goat IgG could be detected at 25 ng/mL. However, in routine use of a series of coverslips (n>5), 50 ng/mL was the minimal concentration that could be consistently detected with reliability in our device. Concentrations of 100 ng/mL and higher were easily detected for all antigens examined, as shown in FIG. 3.

Obviously, many modifications and variations of the present invention are possible in light of the above teachings. It is therefore to be understood that, within the scope of the appended claims, the invention may be practiced otherwise than as specifically described.

What is claimed is:

1. A chemical sensor for detecting a plurality of analytes in a sample, said sensor comprising:

a patterned signal layer comprising a two-dimensional array of discrete, optically transparent test sections at known locations thereon, each of said test sections comprising an immobilized specific binding partner for one of said plurality of analytes, such that specific binding of said analyte to said immobilized specific binding partner generates an optical signal in said test section indicative of the presence of said analyte;

a two-dimensional light sensor array which detects said optical signal in a corresponding discrete detection section; and a two-dimensional array of graded index of refraction lenses which focuses each said optical signal from each said test section into each said corresponding detection section.

2. The chemical sensor of claim 1 wherein said patterned signal layer is a waveguide comprising said discrete test sections of said immobilized specific binding partners.

3. The chemical sensor of claim 2 wherein said waveguide is a glass coverslip or a microscope slide.

4. The chemical sensor of claim 1 wherein each of said specific binding partners are antibodies covalently attached to said signal layer, said analytes are antigens, and at least one of said test sections further comprises a conjugate of a detectable label and said antigen or an analog thereof specifically bound to said immobilized antibody.

5. The chemical sensor of claim 4 wherein said detectable label is a fluorescent label and said sensor further comprises:

a light source which irradiates said fluorescent label at a known excitation wavelength such that the fluorescent label emits light at a known emission wavelength to provide said optical signal and a filter positioned between patterned signal layer and said two-dimensional light sensor array, wherein said filter removes transmitted light of the known excitation wavelength before said optical signal is detected by said two-dimensional light sensor array.

6. The chemical sensor of claim 5 wherein said filter is positioned between said two-dimensional lens array and said two-dimensional light sensor array.

7. The chemical sensor of claim 6 wherein said filter is sandwiched directly between said two-dimensional lens array and said two-dimensional light sensor array.

8. The chemical sensor of claim 1 wherein said two-dimensional light sensor array is a charge-coupled device array.

9. The chemical sensor of claim 1 wherein said two-dimensional array of graded index of refraction lenses is positioned between said patterned signal layer and said two-dimensional light sensor array.

10. A method of simultaneously detecting a plurality of analytes in a sample, comprising:
(a) providing a chemical sensor, said sensor comprising:
a patterned signal layer comprising a two-dimensional array of discrete, optically transparent test sections at known locations thereon, each of said test sections comprising an immobilized specific binding partner for one of said plurality of analytes, such that specific binding of said analyte to said immobilized specific binding partner generates an optical signal indicative of the presence of said analyte in said test section;
a two-dimensional light sensor array which detects said optical signal in a corresponding discrete detection section; and
a two-dimensional array of graded index of refraction lenses which focuses each said optical signal from each said test section into each said corresponding detection section;
(b) contacting said sample to said patterned signal layer; and
(c) detecting the presence or absence of said focused optical signal in each of said detection sections, whereby the presence of said focused optical signal in said detection section indicates the specific binding of the analyte in the test section and thereby indicates the presence of the analyte in the sample.

11. The method of claim 10 wherein said contacting step further comprises contacting said sample and said patterned signal layer with a labeled reagent comprising a fluorescent label conjugated to (i) either said analyte or an analog thereof which is specifically bound by said immobilized specific binding partner or (ii) a second specific binding partner which specifically binds to said analyte at a site which does not intefere with the specific binding between said analyte and said immobilized specific binding partner.

12. The method of claim 11, wherein said sensor further comprises a light source for irradiating said fluorescent label at a known excitation wavelength such that the fluorescent label emits light at a known emission wavelength to provide said optical signal and said method further comprises a step of irradiating said patterned signal layer with said excitation wavelength after said contacting step, thereby producing the focused optical signal detected in the detecting step.

13. The method of claim 12, wherein said sensor further comprises a filter positioned between patterned signal layer and said two-dimensional light sensor array, wherein said filter removes transmitted light of the known excitation wavelength before said optical signal is detected by said two-dimensional light sensor array and said detecting step further comprises removing said transmitted light of the known excitation wavelength before detecting said focused optical signal.

14. The method of claim 10 wherein said two-dimensional light sensor array is a charge-coupled device array.

15. A method of simultaneously detecting a plurality of analytes in a sample, comprising:
(a) providing a chemical sensor, said sensor comprising:
a patterned signal layer comprising a two-dimensional array of discrete, optically transparent test sections at known locations thereon, each of said test sections comprising an immobilized antibody which specifically binds to one of said plurality of analytes such that the specific binding generates an optical signal indicative of the presence of said analyte in said test section;
a two-dimensional light sensor array which detects said optical signal in a corresponding discrete detection section;
a two-dimensional array of graded index of refraction lenses which focuses each said optical signal from each said test section into each said corresponding detection section; and,
a light source for irradiating a fluorescent label at a known excitation wavelength such that the fluorescent label emits light a known emission wavelength to provide said optical signal;
(b) contacting said sample, said patterned sign layer and a labeled reagent comprising said fluorescent label conjugated to (i) either said analyte or an analog thereof which is specifically bound by said immobilized antibody or (ii) a second antibody which specifically binds to said analyte at a site which does not interfere with the specific binding between said analyte and said immobilized antibody;
(c) irradiating said patterned signal layer with said excitation wavelength after said contacting step, thereby producing said focused optical signal; and
(d) detecting the presence or absence of said focused optical signal in each of said detection sections, whereby the presence of said focused optical signal indicates the specific binding of the analyte in the test section and thereby indicates the presence of the analyte in the sample.

* * * * *